United States Patent [19]
Smith et al.

[11] Patent Number: 5,935,076
[45] Date of Patent: Aug. 10, 1999

[54] METHOD AND APPARATUS FOR ACCURATELY MEASURING THE TRANSMITTANCE OF BLOOD WITHIN A RETINAL VESSEL

[75] Inventors: Matthew H. Smith; Russell A. Chipman, both of Madison, Ala.; Thomas E. Minnich, North Little Rock, Ark.; Lloyd W. Hillman, Huntsville; Kurt R. Denninghoff, Birmingham, both of Ala.

[73] Assignee: University of Alabama in Huntsville, Huntsville, Ala.

[21] Appl. No.: 08/797,414

[22] Filed: Feb. 10, 1997

[51] Int. Cl.⁶ ........................................... A61B 5/00
[52] U.S. Cl. .................... 600/479; 600/504; 600/310; 356/41
[58] Field of Search ................... 600/479, 504, 600/558, 318, 319, 320, 310; 356/41; 351/206, 221

[56] References Cited

U.S. PATENT DOCUMENTS

| | | |
|---|---|---|
| 3,847,483 | 11/1974 | Shaw et al. . |
| 4,114,604 | 9/1978 | Shaw et al. . |
| 4,166,695 | 9/1979 | Hill et al. . |
| 4,253,744 | 3/1981 | Sawa . |
| 4,305,398 | 12/1981 | Sawa . |
| 4,346,991 | 8/1982 | Gardner et al. .................. 356/28.5 |
| 4,350,163 | 9/1982 | Ford, Jr. et al. . |
| 4,485,820 | 12/1984 | Flower . |
| 4,579,430 | 4/1986 | Bille . |
| 4,694,833 | 9/1987 | Hamaguri . |
| 4,697,593 | 10/1987 | Evans et al. . |

(List continued on next page.)

OTHER PUBLICATIONS

Hickam, John B., Frayser, Regina, Ross, Joseph C., A Study Of Retinal Venous Blood Oxygen Saturation In Human Subjects By Photographic Means, *Circulation*, vol. XXVII, Mar. 1963, pp. 375–384.

Van Assendelft, O.W., *Spectrophotometry Of Haemoglobin Derivatives*, Thomas, Springfield, IL 1970), pp. 55–59.

Laing, R.A., Danisch, L.A., Young, L.R., The Choroidal Eye Oximeter: An Instrument For Measuring Oxygen Saturation Of Choroidal Blood In Vivo, *IEEE Transactions On Biomedical Engineering*, vol. BME–222, No. 3, May 1975, pp. 183–195.

Cohen, Allen J., Laing, Ronald A., Multiple Scattering Analysis Of Retinal Blood Oximetry, *IEEE Transactions On Biomedical Engineering*, vol. BME–23, No. 5, Sep. 1976, pp. 391–399.

(List continued on next page.)

*Primary Examiner*—Marvin M. Lateef
*Assistant Examiner*—Eleni Mantis Mercader
*Attorney, Agent, or Firm*—Bell Seltzer Intellectual Property Law Group of Alston & Bird LLP

[57] ABSTRACT

The method and apparatus for measuring the transmittance of blood within a retinal vessel detects the intensity of light reflected from illuminated portions of an eye, including the retinal vessel and background fundus, and adjusts the corresponding intensity signals to compensate for reflections from the retinal vessel. In particular, the transmittance measuring method and apparatus constructs an intensity profile function based upon the intensity signals. As a result, the intensity profile function approximates the intensity of light transmitted through the retinal vessel as a function of retinal vessel position. During the construction of the intensity profile function, the transmittance measuring method and apparatus can compensate for at least some of the reflections of light from the retinal vessel which occurred prior to propagation of the light through the retinal vessel, thereby increasing the accuracy with which the transmittance of blood within a retinal vessel is measured. In addition, the transmittance measuring method and apparatus can compensate for the finite point spread function of the light with which the eye is illuminated in order to further increase the resulting measurement accuracy.

39 Claims, 6 Drawing Sheets

U.S. PATENT DOCUMENTS

| | | |
|---|---|---|
| 4,824,242 | 4/1989 | Frick et al. . |
| 4,836,207 | 6/1989 | Bursell et al. . |
| 4,838,683 | 6/1989 | Ichihashi et al. . |
| 4,859,056 | 8/1989 | Prosser et al. . |
| 4,869,254 | 9/1989 | Stone et al. . |
| 4,877,322 | 10/1989 | Hill . |
| 4,907,876 | 3/1990 | Suzuki et al. . |
| 4,922,919 | 5/1990 | Novack . |
| 4,941,741 | 7/1990 | Mizuta . |
| 4,942,877 | 7/1990 | Sakai et al. . |
| 5,078,136 | 1/1992 | Stone et al. . |
| 5,119,814 | 6/1992 | Minnich . |
| 5,219,400 | 6/1993 | Jacot et al. . |
| 5,246,002 | 9/1993 | Prosser . |
| 5,285,782 | 2/1994 | Prosser . |
| 5,297,554 | 3/1994 | Glynn et al. . |
| 5,308,919 | 5/1994 | Minnich . |
| 5,318,022 | 6/1994 | Taboada et al. . |
| 5,377,674 | 1/1995 | Kuestner . |
| 5,433,197 | 7/1995 | Stark . |
| 5,515,864 | 5/1996 | Zuckerman . |
| 5,517,987 | 5/1996 | Tsuchiya . |
| 5,524,617 | 6/1996 | Mannheimer . |
| 5,640,963 | 6/1997 | Tanaka ..................................... 128/665 |

OTHER PUBLICATIONS

Roberts, D. Aaron, Analysis Of Vessel Absorption Profiles In Retinal Oximetry, *Medical Physics*, vol. 14, No. 1, Jan./Feb. 1987, pp. 124–130.

Delori, Francois C., Noninvasive Technique For Oximetry Of Blood In Retinal Vessels, *Applied Optics*, vol. 27, Mar. 15, 1988, pp. 1113–1125.

METHOD AND APPARATUS FOR ACCURATELY MEASURING THE TRANSMITTANCE OF BLOOD WITHIN A RETINAL VESSEL

BACKGROUND OF THE INVENTION

The present invention relates generally to methods and apparatus for measuring the transmittance of blood within a retinal vessel and, more particularly, to methods and apparatus for accurately measuring the transmittance of blood within a retinal vessel by compensating for specular reflections from the apex of the retinal vessel and, in some embodiments, from edge portions of the retinal vessel.

A variety of spectroscopic oximetry techniques have been developed to monitor the transmittance of a blood sample. The transmittance of a blood sample is an important parameter since a number of other physiological parameters can be determined based upon the transmittance of a blood sample. For example, the absorbance of the blood sample and, in turn, the optical density of the blood sample can be readily determined based upon the transmittance of the blood sample. In addition, the blood oxygen saturation can be determined based upon the transmittance of the blood sample. By monitoring the blood oxygen saturation, the arteriovenous oxygen difference can be determined as described by U.S. Pat. No. 5,308,919 to Thomas E. Minnich. Based upon the arteriovenous oxygen difference, changes in the cardiac output of a patient can be determined to assist the post-operative monitoring and the management of critically ill patients. By monitoring the blood oxygen saturation, the loss of blood can also be detected and the rate and quantity of blood loss over time can be estimated as described in U.S. Pat. No. 5,119,814 to Thomas E. Minnich.

Conventional spectroscopic oximetry techniques measure the transmittance of a blood sample by illuminating the blood sample and measuring the intensity of the light which is transmitted through the blood sample. Based upon the intensity of the transmitted light, the transmittance of the blood sample can be determined.

These conventional spectroscopic oximetry techniques analyze blood that has been drawn from a patient and is disposed within a cuvette. Accordingly, the thickness of the sample and the concentration of the sample can be controlled to reduce the error in the measured transmittance. However, these spectroscopic oximetry techniques do require blood to be drawn from a patient to be analyzed. To develop a time history of the transmittance of a patient's blood so as to detect trends or changes in the transmittance of the blood over time, these conventional spectroscopic oximetry techniques require blood samples to be repeatedly drawn from a patient. In addition to the discomfort of the patient from which the blood is drawn, it quickly becomes a laborious and time consuming task to repeatedly draw blood samples from a patient and then to analyze each of the samples to determine the transmittance of the patient's blood over time. In addition, the transmittance of the blood cannot be analyzed in real time since the blood sample must be drawn and processed prior to measuring the transmittance of the blood sample.

Accordingly, a number of non-invasive retinal oximeters have been developed to measure the transmittance of the blood within a retinal vessel of a patient, thereby allowing a patient's blood to be analyzed in a non-invasive manner. For example, a retinal oximeter based upon photographic techniques is described by Dr. John B. Hickham, et al., in an article entitled A Study Of Retinal Venous Blood Oxygen Saturation In Human Subjects by Photographic Means, *Circulation*, Vol. 27, pp. 375–84 (March 1963). The retinal oximeter proposed by Hickham illuminates a retinal vessel with light having two different pairs of wavelengths, namely, light having a red/green pair of wavelengths, such as 640 nm and 510 nm, and light having a red/infrared pair of wavelengths such as 640 nm and 800 nm. The retinal oximeter proposed by Hickham also includes a fundus camera for exposing images of the illuminated optic nerve head directly to film. Once developed, the film density was measured at the center of a retinal vessel as well as on either side of the retinal vessel. For example, the film density can be measured, such as with a microdensitometer. Thus, the film density of the retinal vessel as well as the film density of the optic disk was measured.

By subtracting the film density of the retinal vessel from the film density of the optic disk, the retinal oximeter proposed by Hickham obtains a value proportional to the optical density of the retinal vessel. Since the light had actually propagated through the retinal vessel twice prior to being captured by the fundus camera, Hickham also proposed that the optical density of the retinal vessel obtained in the manner described above was actually equal to twice the actual optical density of the blood within the retinal vessel. See A. J. Cohen, et al., Multiple Scattering Analysis Of Retinal Blood Oximetry, *IEEE, Trans. On Biomedical Engineering*, Vol. 23, No. 5, pp. 391–400 (September 1976) which also describes a photographic eye oximeter which employs a modified fundus camera to obtain images of a retinal vessel at two different wavelengths of light, such as 470 nm and 515 nm.

As known to those skilled in the art, the light with which a retinal vessel is illuminated is not only transmitted through and absorbed within the retinal vessel, but is also specularly reflected from both the retinal vessel and the retinal background, such as the background fundus, on either side of the retinal vessel. If a significant portion of the light is reflected from either the retinal vessel or the background fundus on either side of the retinal vessel, the film density of the resulting image of the retinal vessel will not accurately depict the transmittance of the blood within the retinal vessel. Since the retinal oximeters proposed by Hickham and Cohen provide an image of a large portion of the retina, the operator of the retinal oximeter was able to select those portions of the resulting image which were least affected by specular reflections from either the retinal vessel or the background fundus. However, retinal oximeters based on photographic techniques, such as the retinal oximeters proposed by Hickham and Cohen are relatively difficult to automate since these techniques depend, at least in part, upon the operator's selection of the appropriate portion of the resulting image for analysis to determine a transmittance measurement which is not adversely affected by specular reflections from the retinal vessel or from the background fundus on either side of the retinal vessel.

Accordingly, scanning retinal oximeters have been developed to measure the transmittance of blood within a retinal vessel in an automated fashion. See, for example, U.S. Pat. No. 5,308,919 to Thomas E. Minnich which describes an eye oximeter for determining the arteriovenous oxygen difference by scanning the optic disk of a patient in a non-invasive manner.

In addition, F. C. Delori describes another scanning retinal oximeter in an article entitled Noninvasive Technique For Oximetry Of Blood In Retinal Vessels", *Applied Optics*, Vol. 27, No. 6, pp. 1113–25 (Mar. 15, 1988). The retinal vessel oximeter proposed by Delori includes a modified fundus camera which illuminates a retinal vessel with light having three wavelengths, such as 569.8 nm, 559.3 nm and 586.5 nm. The retinal vessel oximeter proposed by Delori scans the light across a retinal vessel and measures the intensity of the light transmitted through and reflected from the retinal vessel. As shown in FIG. 1, the intensity measured by the retinal oximeter proposed by Delori can be graphically illustrated as a function of retinal position. Based upon the measured intensity signals, the retinal oximeter proposed by Delori locates the retinal vessel by identifying the rising and falling edges of the intensity signal as the intensity signal crosses a vessel detection level. As shown in FIG. 1, the vessel detection level is typically set to seven-eighths of the mean value of the intensity signals measured by the retinal oximeter.

As also shown in FIG. 1, points b and g represent the points having the largest negative slope and the largest positive slope, respectively. Points a and h of FIG. 1 represent the boundary between the retinal vessel and the background fundus. Points a and h are typically determined as those points at which the absolute value of the slope of the signal intensity function becomes less than one-eighth of the absolute values of the minimum slope at point b and the maximum slope at point g, respectively. In addition, points d and e represent points having the minimum intensity within the retinal vessel. As discussed hereinafter, the upturned portion of the signal intensity graph between points d and e typically represents a specular reflection from the apex of the retinal vessel which can significantly diminish the accuracy with which a retinal oximeter determines the transmittance of a retinal vessel. As also shown in FIG. 1, points c and f are halfway between points b and d and points e and g, respectively.

The retinal oximeter proposed by Delori initially determines an average intensity value for the light reflecting from the background fundus by determining the average value of the intensity signals to the left of point a and to the right of point h. In other words, the retinal oximeter proposed by Delori determines the average intensity value for Region I of FIG. 1. In addition, the retinal oximeter proposed by Delori determines the average intensity of the light transmitted through the retinal vessel by determining the average value of the intensity signals between points c and d and between points e and f, i.e., the average value of the intensity signals within region II. As a result, the retinal oximeter proposed by Delori determines the transmittance of the blood within retinal vessel by dividing the average intensity of light transmitted through the retinal vessel by the average intensity of the light reflected from the background fundus.

Even though the retinal oximeter proposed by Delori determines the transmittance of blood within a retinal vessel in an automated fashion, the retinal oximeter proposed by Delori typically requires a relatively large number of scans to accurately determine the average values of the intensity of light transmitted through the retinal vessel and the intensity of light reflected from the background fundus. In addition, the retinal oximeter proposed by Delori generally requires a relatively large difference in contrast between the retinal vessel and the background fundus. It has been determined for light having many of the wavelengths useful for retinal oximetry, however, that the blood in relatively large retinal veins typically absorbs only about 15%. of the incident light, while the blood in relatively large retinal arteries absorbs only about 10% or less of the incident light. In addition, variations in the retinal pigmentation and the presence of underlying choroidal vessels frequently create variations in the intensity of the light reflected from the background fundus which are more pronounced than the variations in the intensity of the light transmitted through a retinal vessel. As a result, the retinal oximeter proposed by Delori which identifies a retinal vessel based upon a predetermined vessel detection threshold may not properly identify a retinal vessel and, as a result, may not accurately measure the transmittance of the retinal vessel.

As described above, it is oftentimes desirable to measure the transmittance of a blood sample in an accurate and timely manner. A number of invasive and non-invasive spectroscopic oximetry techniques have therefore been developed for determining the transmittance of a blood sample. However, a non-invasive retinal oximeter for determining the transmittance of the blood within a retinal vessel has not yet been developed which reduces or minimizes the errors in the measured transmittance which arise from specular reflections from the apex of the retinal vessel or from the opposed edge portions of the retinal vessel.

SUMMARY OF THE INVENTION

It is therefore an object of the present invention to provide an improved method and apparatus for measuring the transmittance of blood within a retinal vessel in an non-invasive manner.

It is another object of the present invention to provide a method and apparatus for measuring the transmittance of blood within a retinal vessel with increased precision and accuracy.

It is the further object of one embodiment of the present invention to provide a method and apparatus for compensating for specular reflections from the retinal vessel, such as from the central portion or the opposed edge portions of the retinal vessel, to measure the transmittance of the blood within the retinal vessel in an accurate manner.

These and other objects are provided, according to the present invention, by a method and apparatus for measuring the transmittance of blood within a retinal vessel based upon intensity signals representing the intensity of light reflected from illuminated portions of the eye which, in one advantageous embodiment, have been adjusted to compensate for reflections from the retinal vessel. For example, the transmittance measuring apparatus can include a computer program product having a computer-readable storage medium including computer-readable program code means for determining the transmittance of blood within the retinal vessel according to the present invention.

Regardless of the implementation, the transmittance measuring method and apparatus constructs an intensity profile function based upon the intensity signals representing the intensity of light reflected from illuminated portions of the eye. As a result, the intensity profile function approximates the intensity of light transmitted through the retinal vessel as a function of retinal vessel position. During the construction of the intensity profile function, the transmittance measuring method and apparatus of one advantageous embodiment compensates for at least some of the reflections of light from the retinal vessel which occurred prior to propagation of the light through the retinal vessel, thereby increasing the accuracy with which the transmittance measuring method and apparatus can measure the transmittance of blood within a retinal vessel. Since the incident light is typically defined by a finite point spread function, the transmittance measuring method and apparatus can also compensate for the finite point spread function in order to further increase the accuracy with which the transmittance of blood within the retinal vessel is determined.

In order to measure the transmittance of the blood within a retinal vessel according to the present invention, the transmittance measuring method and apparatus also determines the intensity of light reflected from the background fundus based upon corresponding intensity signals. For example, the transmittance measuring method and apparatus of one advantageous embodiment constructs a second intensity profile function based upon the intensity signals representing the intensity of light reflected from the background fundus to approximate the intensity of light reflected from the background fundus as a function of retinal position. During the construction of the second intensity profile function, the transmittance measuring method and apparatus may compensate for reflections of light at opposed edge portions of the retinal vessel to more accurately represent the intensity of light reflected from the background fundus.

Based upon the intensity profile function and the intensity of light reflected from the background fundus as most commonly represented by a second intensity profile function, the transmittance measuring method and apparatus determines the transmittance of blood within the retinal vessel. In particular, the transmittance measuring method and apparatus of one advantageous embodiment divides the intensity profile function by the second intensity profile function to form an intermediate transmittance function. The method and apparatus of this advantageous embodiment then determines a minimum value of the intermediate transmittance function which corresponds to the transmittance of the blood within the retinal vessel.

In constructing the intensity profile function, the transmittance measuring method and apparatus determines the intensity of light transmitted through the lateral portions of the retinal vessel. The transmittance measuring method and apparatus of this embodiment also compensates for reflections of light from a central portion of the retinal vessel which occur prior to propagation of light through the retinal vessel. In particular, the transmittance measuring method and apparatus creates the intensity profile function based upon the intensity signals representing the intensity of light transmitted through the lateral portions of the retinal vessel such that the intensity profile function approximates the light transmitted through the central portion of the retinal vessel in the absence of reflections from the central portion of the retinal vessel.

In order to determine the intensity of light transmitted through lateral portions of the retinal vessel, the transmittance measuring method and apparatus of one advantageous embodiment approximates a portion of the intensity profile function which describes the intensity of light transmitted through lateral portions of the retinal vessel as a function of retinal vessel position. The transmittance measuring method and apparatus of this advantageous embodiment can then fit a curve to the portion of the intensity profile function describing the intensity of light transmitted through lateral portions of the retinal vessel as a function of retinal vessel position. As a result, the fitted curve defines the intensity profile function. For example, the transmittance measuring method and apparatus of this embodiment can fit a substantially U-shaped curve, such as a third order function, to the portion of the intensity profile function describing the intensity of light transmitted through lateral portions of the retinal vessel as a function of retinal vessel position.

According to one advantageous embodiment, the transmittance measuring apparatus includes an optical source for illuminating the retinal vessel and at least a portion of the background fundus. The transmittance measuring apparatus of this advantageous embodiment can also include a detector for detecting the intensity of light reflected from illuminated portions of the eye and for providing corresponding intensity signals. Prior to constructing the intensity profile function based upon the intensity signals, the transmittance measuring method and apparatus of one advantageous embodiment identifies a portion of the intensity signals as corresponding to light which has propagated through a retinal vessel. For example, the transmittance measuring method and apparatus of this embodiment may match a portion of the intensity signals with a predetermined pattern corresponding to the intensity signals generated by light propagating through a retinal vessel of a known size.

Once the intensity signals corresponding to light which has propagated through a retinal vessel are identified, the transmittance measuring method and apparatus can determine an intensity profile function which compensates for reflections from the central portions of the retinal vessel and, in turn, can determine the transmittance of the blood within the retinal vessel. By compensating for reflections from the central portion of the retinal vessel and, in some embodiments, for reflections from the opposed edge portions of the retinal vessel, the transmittance measuring method and apparatus more precisely measures the transmittance of the blood within the retinal vessel. As a result, the other physiological parameters which can be determined based upon the transmittance measurement can also be more precisely defined, thereby permitting more accurate diagnosis and treatment of patients.

According to another advantageous embodiment, blood within a retinal vessel can be analyzed by providing a mathematical model of the intensity of light transmitted through the retinal vessel as a function of retinal vessel position. According to this embodiment, the mathematical model includes a plurality of parameters including parameters describing the retinal vessel and parameters describing reflections of light from the retinal vessel which occurred prior to propagation of the light through the retinal vessel. The mathematical model is then fit to the intensity profile function. For example, the mathematical model typically defines a nonlinear curve which is fit to the intensity profile function. Based upon the fit of the mathematical model to the intensity profile function, the method of this advantageous embodiment can then determine at least one parameter describing the retinal vessel, such as the transmittance of blood within the retinal vessel or the diameter of the retinal vessel.

Accordingly, the method of this alternative embodiment also determines retinal vessel parameters, such as the transmittance of blood within the retinal vessel, in an accurate manner by accounting for reflections from the retinal vessel in the mathematical model. As a result, the other physiological parameters which can be determined based upon the transmittance of blood within the retinal vessel can also be more precisely defined.

BRIEF DESCRIPTION OF THE DRAWING

Some of the objects and advantages of the present invention have been stated, others will appear as the description proceeds when taken in conjunction with the accompanying drawings, which are not necessarily drawn to scale, wherein.

DETAILED DESCRIPTION OF THE PREFERRED EMBODIMENTS

The present invention now will be described more fully hereinafter with reference to the accompany drawings, in which a preferred embodiment of the invention is shown. The invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
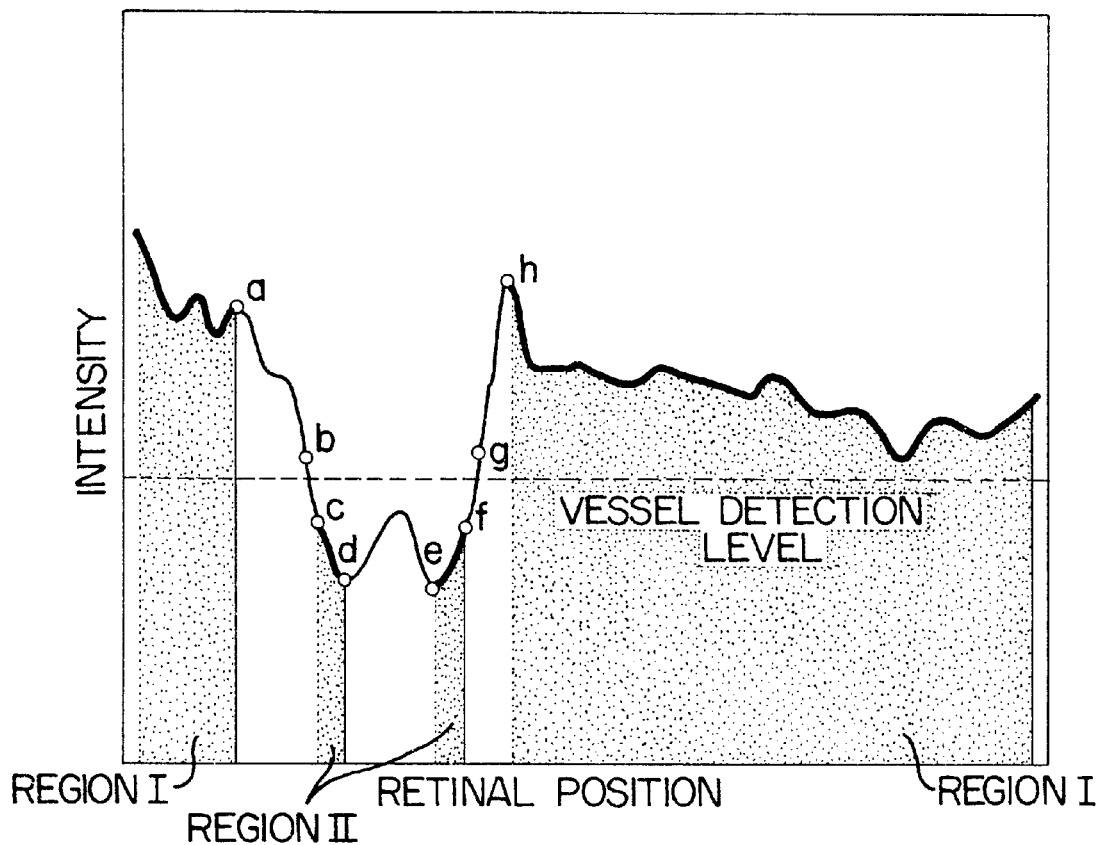
FIG. 1 is a graphical representation of an intensity profile function on which several points and regions have been identified which are utilized by the prior art retinal oximeter proposed by Delori.
Figure 2:
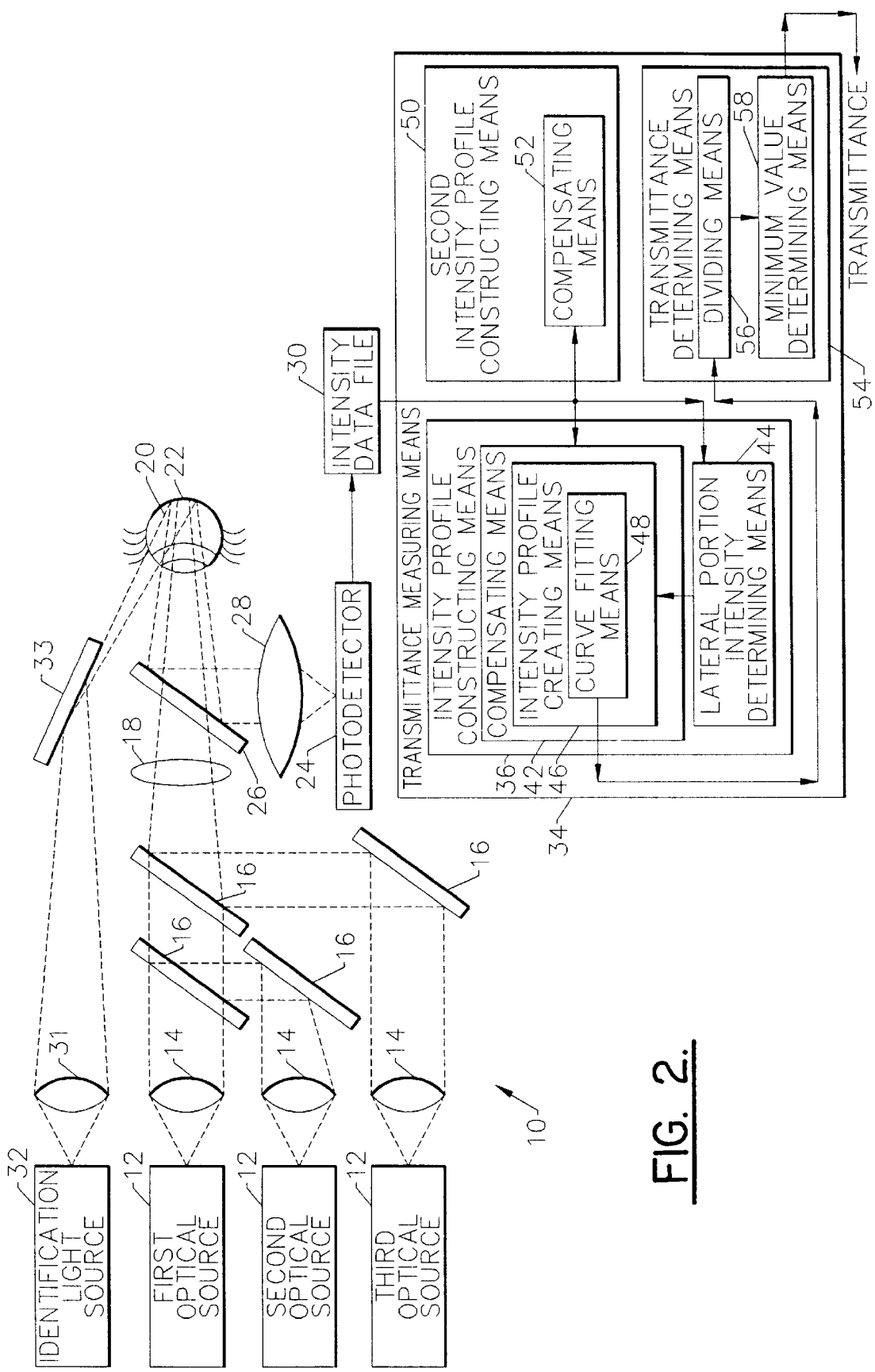
FIG. 2 is a block diagram illustrating one embodiment of the method and apparatus for measuring the transmittance of blood within a retinal vessel according to the present invention.

Referring now to FIG. 2, an apparatus 10 for analyzing the blood within a retinal vessel, such as by measuring the transmittance of blood within the retinal vessel, in a non-invasive manner is illustrated. By monitoring the transmittance of the patient's blood, physicians and other health care personnel can track a number of physiological parameters and can determine, among other things, the patient's blood loss and/or changes in the patient's cardiac output.

Figure 6:
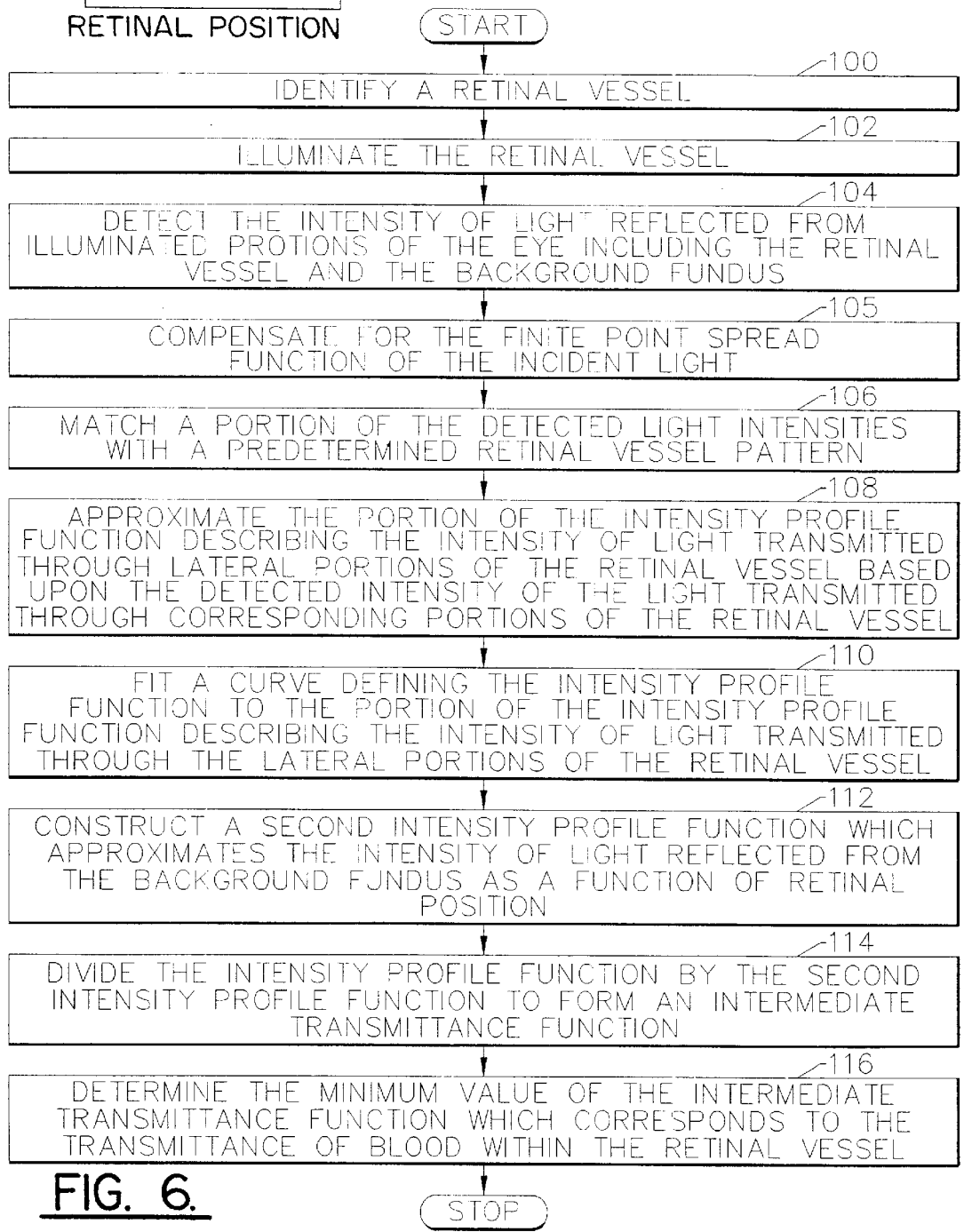
FIG. 6 is a flowchart illustrating the operations performed by one embodiment of the method and apparatus for measuring the transmittance of blood within a retinal vessel according to the present invention.
Figure 7:
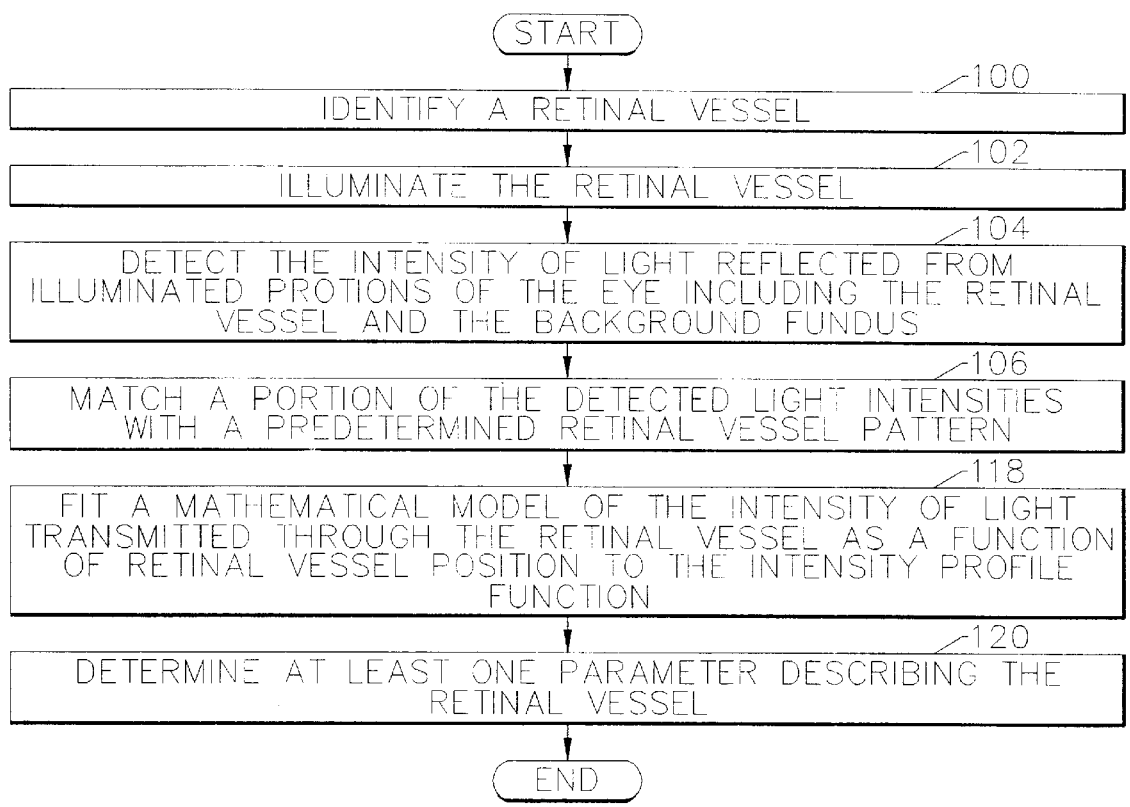
FIG. 7 is a flowchart illustrating the operations performed by another embodiment of the method and apparatus for analyzing blood within a retinal vessel according to the present invention.

As shown in FIG. 2 and in block 102 of FIGS. 6 and 7, a transmittance measuring apparatus 10 of one embodiment of the present invention includes an optical source 12 for illuminating the retinal vessel and at least a portion of the background fundus. The optical source typically illuminates a retinal vessel with light having either two or three different wavelengths. However, the optical source can illuminate the retinal vessel with light having any number of wavelengths without departing from the spirit and scope of the present invention. For purposes of illustration, however, FIG. 2 illustrates a transmittance measuring apparatus according to one embodiment of the present invention in which three optical sources, such as three lasers, illuminate the retinal vessel with light having three different wavelengths, such as 493 nm, 635 nm and 960 nm.

The optical signals provided by each optical source 12 are generally focused, such as by respective lens elements 14. In addition, the focused optical signals provided by each optical source are typically combined, such as by one or more being combiners 16, to form a composite beam of light 18 having each of the different respective wavelengths.

As shown in FIG. 2, the composite beam of light 18 is directed to impinge upon the retina 22 of a patient's eye 20, including a retinal vessel, such as a retinal vein or a retinal artery, and at least a portion of the background fundus. In particular, the transmittance measuring method and apparatus 10 preferably scans the composite beam across a retinal vessel and a portion of the background fundus. As known to those skilled in the art, a retinal vessel reflects, absorbs and transmits light of each of the different wavelengths in a quantitatively different manner than the background fundus. In addition, the blood within a retinal vessel absorbs and transmits light of each of the different wavelengths in a quantitatively different manner depending upon the level of oxygen saturation of the blood. In other words, oxyhemoglobin and desaturated hemoglobin each absorb and reflect light having a non-isobestic wavelength in a different manner.

The transmittance measuring apparatus 10 also includes a detector 24, such as a photodetector, for measuring the intensity of light reflected from illuminated portions of the eye, including light reflected from the retinal vessel and the background fundus. See block 104 of FIGS. 6 and 7. As shown in FIG. 2, the transmittance measuring apparatus can also include a beam splitter 26 and a focusing lens 28 to direct the light that has been reflected from the illuminated portions of the eye to the detector.

Based upon the intensity of the detected light as the composite beam 18 is scanned, the detector 24 provides corresponding intensity signals. The intensity signals represent the intensity of light reflected from illuminated portions of the eye. As shown in FIG. 2, the transmittance measuring apparatus 10 preferably includes a memory device, such as random access memory (RAM), for storing the intensity signals such as in an intensity data file 30.

Based upon the intensity signals provided by the detector 24, the transmittance measuring method and apparatus 10 can readily determine the transmittance of blood within the retinal vessel. As known to those skilled in the art, the transmittance of the blood within a retinal vessel to light of a selected wavelength is mathematically related to the oxygen saturation of the blood, as well as a number of other physiological parameters. Thus, the oxygen saturation of the blood as well as several other physiological parameters can also be readily determined based upon the measured transmittance. Since the method and apparatus of the present invention measures the transmittance in a more precise fashion as described below, the oxygen saturation of the blood as well as the other physiological parameters based upon the blood can also be more accurately determined.

In order to properly illuminate a retinal vessel, the transmittance measuring method and apparatus 10 may initially identify a retinal vessel as shown in block 100 of FIGS. 6 and 7. In this regard, the transmittance measuring apparatus can include an identification light source 32 and, in some embodiments, associated focusing and directing elements, such as a focusing lens 31 and a reflector 33, for illuminating a portion of the retina 22 with light having a wavelength which is absorbed in significantly different percentages by a retinal vessel and by the background fundus. For example, the transmittance measuring apparatus can include an identification laser which illuminates a portion of the retina with green light since retinal vessels absorb a much greater percentage of green light than the background fundus. See, for example, U.S. Pat. No. 5,308,919 to Thomas E. Minnich. By examining the intensity signals produced by the detector 24 in response to illumination of the retina by the identification light source, the transmittance measuring method and apparatus of this advantageous embodiment can detect a retinal vessel due to their relatively high absorbance of green light. Thereafter, the transmittance measuring method and apparatus can scan the composite beam 18 across those portions of the retina in which a retinal vessel has been identified.

The transmittance measuring method and apparatus 10 also includes means 34 for measuring the transmittance of blood within a retinal vessel based upon the intensity signals representing the intensity of light reflected from illuminated portions of the eye, including the retinal vessel and the background fundus. In one advantageous embodiment, the means for measuring the transmittance of blood within a retinal vessel includes a computer program product. The computer program product includes a computer-readable storage medium having computer-readable program code means, such as a series of computer instructions, embodied in the computer-readable storage medium for measuring the transmittance of blood within a retinal vessel based upon the intensity signals.

In this regard, FIGS. 2, 6 and 7 are block diagram, flowchart and control flow illustrations of methods, systems and program products according to the invention. It will be understood that each block or step of the block diagram, flowchart and control flow illustrations, and combinations of blocks in the block diagram, flowchart and control flow illustrations, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagram, flowchart or control flow illustrations, and combinations of blocks or steps in the block diagram, flowchart or control flow illustrations, can be implemented by special purpose hardware-based computer systems which perform the specified functions or steps, or combinations of special purpose hardware and computer instructions.

In order to measure the transmittance of blood within a retinal vessel, the transmittance measuring method and apparatus 10 includes means 36 for constructing an intensity profile function based upon the intensity signals representing the intensity of light reflected from illuminated portions of the eye, including the retinal vessel and portions of the background fundus. By way of example, the intensity signals provided by a detector 24 representing the intensity of light reflected from illuminated portions of the eye are shown as a function of retinal position by the solid line in FIG. 3A. As explained hereinafter, the intensity signals to the left of point a and to the right of point f represent reflections from the background fundus. Conversely, the intensity signals between points a and f represent light which has been transmitted through and reflected from the retinal vessel. Based upon the intensity signals, the transmittance measuring method and apparatus constructs the intensity profile function which typically approximates the intensity of light transmitted through, not reflected from, the retinal vessel as a function of retinal vessel position. In this regard, an intensity profile function based upon the intensity signals depicted in solid lines in FIG. 3A is shown by dotted lines.

Figure 3A:
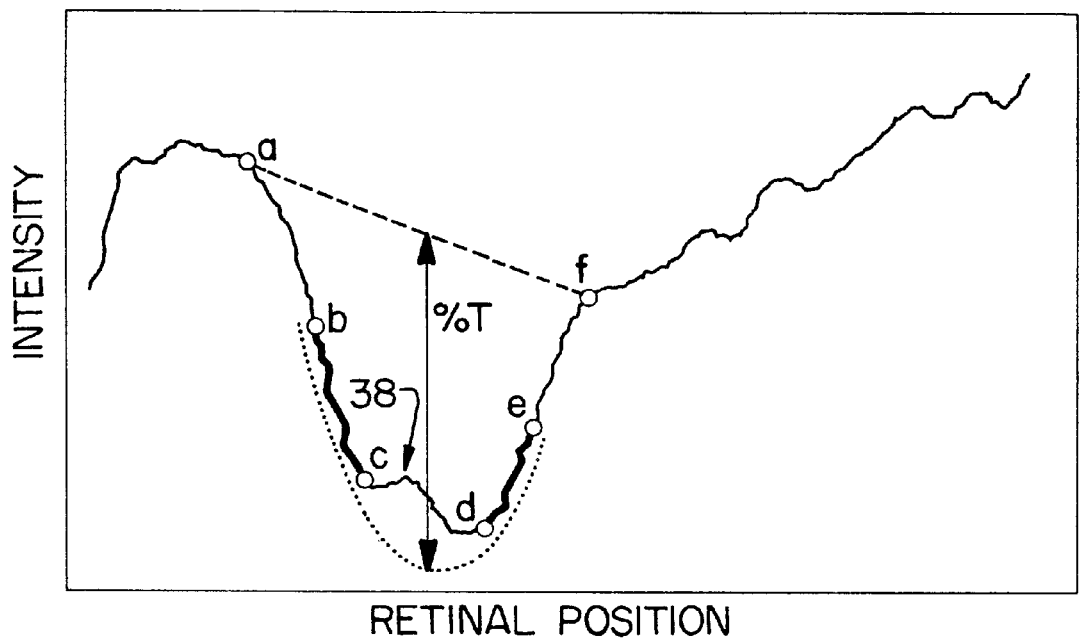
FIGS. 3A and 3B are graphical representations of an intensity profile function and the first derivative of the intensity profile function, respectively, on which several points have been identified which are utilized by the transmittance measuring method and apparatus of one advantageous embodiment of the present invention.
Figure 4A:
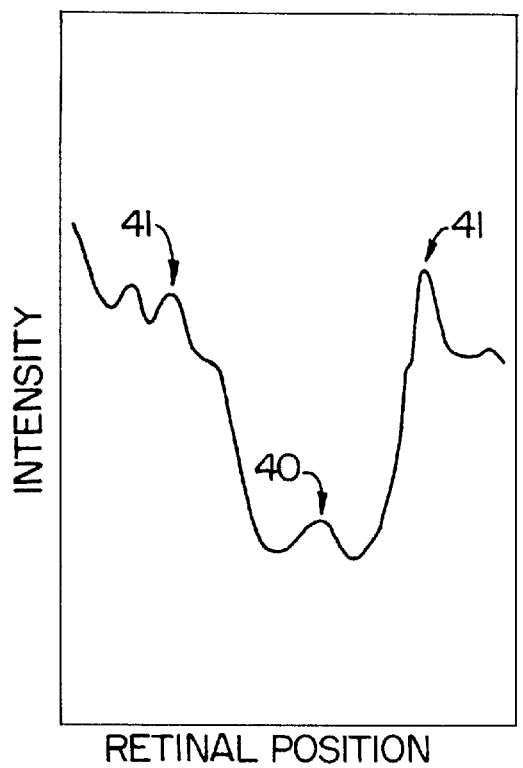
FIGS. 4A and 4B are graphical representations of intensity profile functions which have moderate specular reflections from the retinal vessel and severe specular reflections from the retinal vessel, respectively.
Figure 4B:
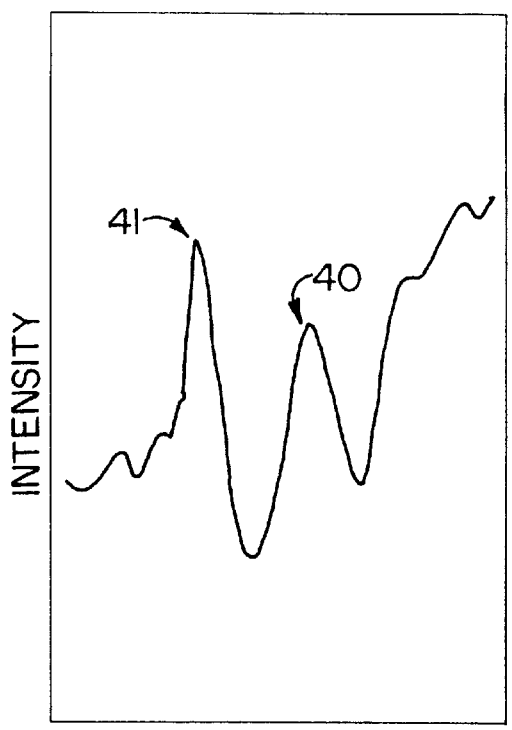

As shown in FIG. 3A, the intensity signals provided by the detector 24 do not accurately represent the intensity of light transmitted through the central portion of the retinal vessel since a significant portion of the light is reflected from the retinal vessel prior to propagating therethrough. For example, the intensity signals represented by the solid line in FIG. 3A include a region 38 of increased relative intensity at a retinal position corresponding to a central portion of the retinal vessel. As a further example, FIGS. 4A and 4B illustrate the intensity signals provided by a detector following a scan of other retinas or other portions of the same retina. As shown by the regions 40 of increased relative intensity at retinal positions corresponding to a central portion of the retinal vessel, the intensity signals of FIG. 4A include moderate reflections from the central portion of the retinal vessels, while the intensity signals of FIG. 4B include more significant reflections from the central portion of the retinal vessel.

According to the present invention, the transmittance measuring apparatus 10 includes means 42 for compensating for at least some of the reflections of light from the retinal vessel and, more particularly, from the central portion of the retinal vessel which occurred prior to the propagation of light through the retinal vessel. As a result of this compensation, the intensity profile function more accurately represents the intensity of light transmitted through the retinal vessel and the transmittance of the blood measured by the method and apparatus of the present invention is determined in a more accurate fashion. For example, the intensity profile function constructed according to the method and apparatus of the present invention and illustrated in dotted lines in FIG. 3A does not include the upturned portion at a position corresponding to the central portion of the retinal vessel but, instead, defines a relatively smooth U-shaped function.

As shown in FIG. 2, the transmittance measuring method and apparatus 10 and, more particularly, the means 36 for constructing the intensity profile function includes means 44 for determining the intensity of light transmitted through lateral portions of the retinal vessel. As shown in FIG. 3A, the intensity signals representing the intensity of light transmitted through the lateral portions of the retinal vessel have not generally been affected by undesirable reflections from the lateral portions of the retinal vessel. As a result, the transmittance measuring method and apparatus and, more particularly, the compensating means 42 includes means 46 for creating the intensity profile function based upon the intensity of light transmitted through the lateral portions of the retinal vessel such that the intensity profile function approximates the light transmitted through the central portion of the retinal vessel in the absence of reflections from the central portion of the retinal vessel.

As used herein, the terms "lateral portions of the retinal vessel" and "central portion of the retinal vessel" do not necessarily refer to the lateralmost portions of the retinal vessel, i.e., the vessel walls, or the centralmost portion of the retinal vessel, respectively. Instead, the terms "lateral portions of the retinal vessel" and "central portion of the retinal vessel" refer to those portions of the retinal vessel which create or give rise to the lateral portions and the central portion of that segment of the intensity signals provided by the detector 24 (see FIG. 3A) which is representative of a retinal vessel.

The means 44 for determining the intensity of light transmitted through lateral portions of the retinal vessel includes means for approximating the portion of the intensity profile function describing the intensity of light transmitted through lateral portions of the retinal vessel based upon the intensity signals representing the intensity of light transmitted through those lateral portions of the retinal vessel. See block 108 of FIG. 6. According to this advantageous embodiment, the intensity profile creating means 46 also includes means 48 for fitting a curve to the portion of the intensity profile function describing the intensity of light transmitted through lateral portions of the retinal vessel as a function of retinal vessel position. See block 110. The resulting curve therefore also defines the intensity profile function shown in dotted lines in FIG. 3A.

The transmittance measuring method and apparatus 10 can fit a variety of curves to the portion of the intensity profile function describing the intensity of light transmitted through lateral portions of the retinal vessel to define the entire intensity profile function. However, the transmittance measuring method and apparatus of one advantageous embodiment fits a U-shaped curve to the portion of the intensity profile function describing the intensity of light transmitted through lateral portions of the retinal vessel. For example, the U-shaped curve can be defined by a cubic equation, namely, $f(x)=c_0+c_1x+c_2x^2+c_3x^3$ wherein x is the retinal position, $f(x)$ is the intensity of the transmitted light and $c_0$, $c_1$, $c_2$ and $c_3$ are constants. Preferably, the curve fitting means 48 defines the curve to minimize or reduce the error between the curve and the portion of the intensity profile function describing the intensity of light transmitted through lateral portions of the retinal vessel. While a curve defined by a cubic equation is described above, the transmittance measuring method and apparatus can fit other types of curves to the portion of the intensity profile function describing the intensity of light transmitted through lateral portions of the retinal vessel without departing from the spirit and scope of present invention.

Figure 3B:
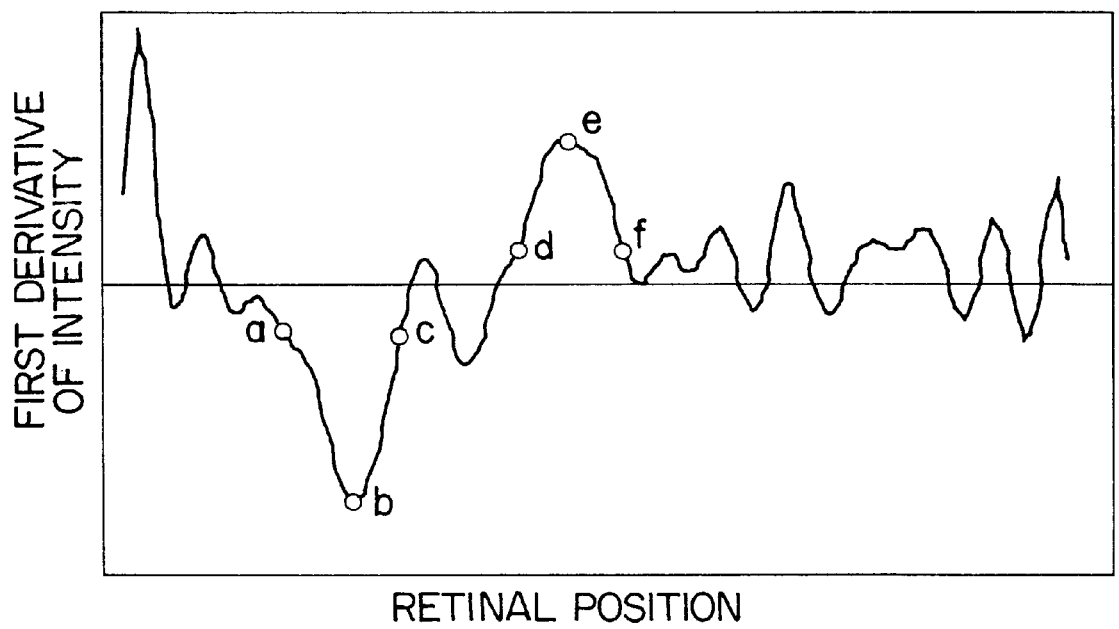

As described above, the intensity signals provided by the detector 24 of one advantageous embodiment in response to the scan of a retina are illustrated as a function of retinal position in FIG. 3A. Correspondingly, FIG. 3B depicts the first derivative or slope of the intensity signals of FIG. 3A as a function of retinal position. As shown, points b and e are the points of minimum and maximum slope, respectively. In addition, points a and c are points at which the slope becomes equal to a predetermined percentage, such as 20%, of the absolute value of the minimum slope at point b, and points d and f are points at which the slope becomes equal to the same predetermined percentage, such as 20%, of the maximum slope at point e.

As described above, the transmittance measuring method and apparatus 10 identifies the portion of the intensity signals represented by the solid lines between points b and c and points d and e as corresponding to the intensity of light transmitted through lateral portions of the retinal vessel. As a result, the transmittance measuring method and apparatus approximates the portion of the intensity profile function describing the intensity of light transmitted through lateral portions of the retinal vessel based upon the intensity signals between points b and c and points d and e. Thus, the curve fitting means preferably fits a curve, such as a curve defined by a cubic function, to the portion of the intensity profile function between points b and c and points d and e since this portion of the intensity signals most accurately represents the transmittance of the light through the retinal vessel. By fitting a curve to the portion of the intensity signals which most accurately represent the light transmitted through the retinal vessel, the transmittance measuring method and apparatus compensates for at least some of the reflections of light from the retinal vessel, such as the reflections of light from the central portion of the retinal vessel, which occurred prior to the propagation of light through the retinal vessel.

According to another embodiment, the transmittance measuring method and apparatus 10 determines the function which most closely matches the intensity signals provided by the detector 24 for all retinal positions. With reference to FIG. 3A, the transmittance measuring method and apparatus of this embodiment would determine a function which most closely matches the intensity signals depicted in solid lines as a function of retinal position. Thereafter, the transmittance measuring method and apparatus of this embodiment constructs an intensity profile function by fitting a curve to that portion of the function which corresponds to the intensity signals transmitted through the lateral portions of the retinal vessel. As a result, the transmittance measuring method and apparatus of this embodiment also compensates for some of the reflections of light from the retinal vessel, such as those reflections of light from the central portion of the retinal vessel.

The transmittance measuring method and apparatus 10 also determines the intensity of light reflected from the background fundus based upon the intensity signals provided by the detector which represent the intensity of light reflected from the background fundus. In this regard, the transmittance measuring method and apparatus preferably includes means 50 for constructing a second intensity profile function which approximates the intensity of light reflected from the background fundus as a function of retinal position. See block 112 of FIG. 6. As illustrated in dashed lines in FIG. 3A, the second intensity profile function can be constructed as a linear function extending between points a and f. As defined above, points a and f represent points at which the first derivative of the intensity signal is a predetermined percentage, such as 20%, of the absolute value of the minimum and maximum slopes, respectively.

The transmittance measuring method and apparatus 10 also includes means 54 for determining the transmittance of blood within the retinal vessel based upon both the intensity profile function and the second intensity profile function. As shown in FIG. 2 and block 114 of FIG. 6, the transmittance measuring method and apparatus includes means 56 for dividing the intensity profile function by the second intensity profile function to form an intermediate transmittance function. The transmittance measuring method and apparatus further includes means 58 for determining a minimum value of the intermediate transmittance function. See block 116. This minimum value corresponds to the transmittance of blood within the retinal vessel and can be thereafter be further processed to determine the oxygen saturation and other physiological parameters related to the transmittance of the blood as known to those skilled in the art. In order to further refine the transmittance measurement, the transmittance measuring method illustrated in FIG. 6 can be repeated several times and the resulting transmittance measurements can be averaged.

It has been observed, however, that light may also reflect from the opposed edge portions of some retinal vessels. For example, light may reflect from that portion of the background fundus which rises to meet the edge portions of the retinal vessels, thereby also degrading the intensity signals provided by the detector 24 which are otherwise representative of the intensity of the light transmitted through the retinal vessel. In particular, light which reflects from the opposed edge portions of a retinal vessel may adversely affect the accuracy with which the transmittance measuring method and apparatus 10 can construct the second intensity profile function approximating the intensity of light reflected from the background fundus as a function of retinal position.

Accordingly, the transmittance measuring method and apparatus 10 and, more particularly, the second intensity profile constructing means 50 preferably includes means 52 for compensating for reflections of light at opposed edge portions of the retinal vessel. In order to compensate for the reflections of light at opposed edge portions of the retinal vessel, the second intensity profile constructing means can adjust points a and f. In one embodiment, the second intensity profile constructing means places points a and f at the second position along the curve representing the actual intensity signals at which the slope of the curve approaches zero. In particular, point a is placed at the second position left of the point b (the point of minimum slope) and point f is placed at the second position right of point e (the point of maximum slope) at which the slope approaches zero.

However, as points a and f are moved outward, i.e., leftward and rightward, respectively, on the curve from points b and e, respectively, the second intensity profile constructing means 50 of one advantageous embodiment will not place points a and f at the second position at which the slope approaches zero if the curve has a ledge prior to reaching a position along the curve at which the slope falls to 20% of the absolute value of the minimum or maximum slope, respectively. Instead, the second intensity profile constructing means of this embodiment will position points a and f at the ledge. In order to detect a ledge, the second intensity profile constructing means can analyze the second derivative of the intensity signals for sign changes which are indicative of a ledge. Once points a and f have been repositioned as described above, the second intensity profile constructing means can construct the second intensity profile function as a line extending through repositioned points a and f.

Figure 5A:
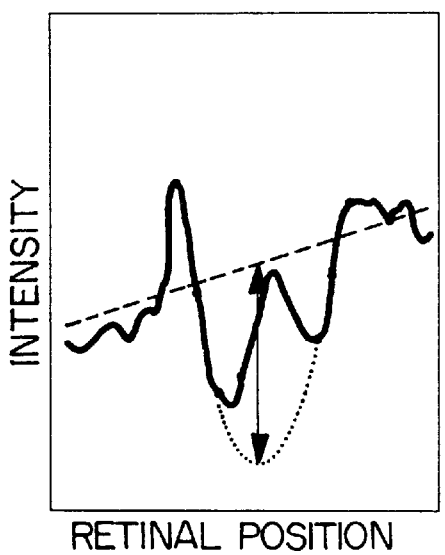
FIGS. 5A–5C are graphical representations of different manners in which the transmittance measuring method and apparatus of the present invention can construct a second intensity profile function to represent the intensity of the light reflected from the background fundus.
Figure 5B:
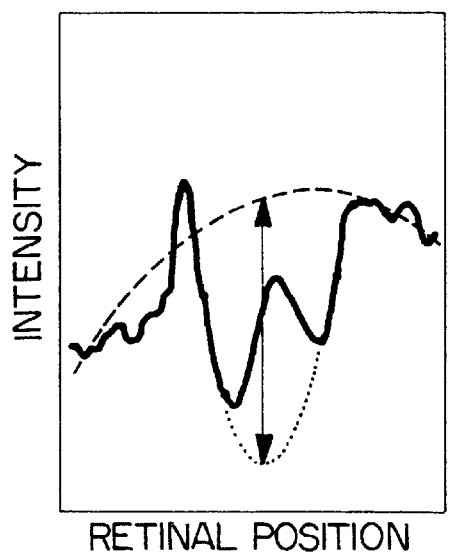
Figure 5C:
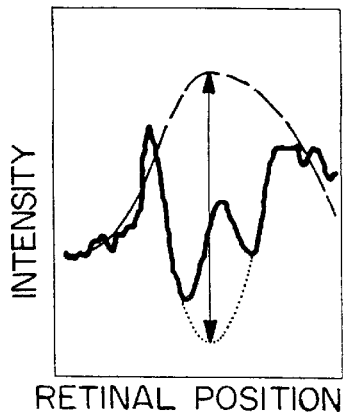

Although the second intensity profile constructing means 50 has been described in conjunction with the construction of a linear function as shown in FIGS. 3A and 5A, the second intensity profile constructing measure can construct a second intensity profile defined by other types of functions, such as a quadratic function as shown in FIG. 5B and a cubic function as shown in FIG. 5C to more accurately represent the intensity of the light reflected from the background fundus and to compensate, if necessary, for undesirable reflections from the opposed edge portions of the retinal vessel.

The optical source 12 generally illuminates the eye with light which is defined by a laser point spread function of a finite size. As a result, the intensity of light reflected from the illuminated portion of the eye as well as the corresponding intensity signals may be somewhat blurred. In order to more accurately determine the transmittance of blood within the retinal vessel, however, the method and apparatus of one advantageous embodiment may compensate for the finite point spread function of the light as shown in blocks 105 of FIG. 6. Although this compensation may be performed by a variety of techniques as will be apparent to those skilled in the art, the method and apparatus of one embodiment performs a deconvolution in the Fourier plane in order to smooth the resulting intensity profile function, prior to fitting curves to the intensity profile function in order to determine the transmittance of blood within the retinal vessel.

According to one advantageous embodiment, the intensity signals provided by the detector 24 can be analyzed initially to identify the portion of the intensity signals which correspond to light that has propagated through a retinal vessel. Since the central portion of a retinal vessel will generally reflects at least some of the incident light, a graph of the resulting intensity signals generally has a "W"-shape in the region corresponding to a retinal vessel. Accordingly, the transmittance measuring method and apparatus 10 of this embodiment can match a predetermined pattern, such as "W"-shaped pattern, with the intensity signals provided by the detector to determine the portion of the intensity signals corresponding to light that has propagated through a retinal vessel. See block 106 of FIGS. 6 and 7. Since retinal vessels have different sizes, the transmittance measuring method and apparatus of this embodiment preferably attempts to match a number of different predetermined patterns with the intensity signals to determine the pattern which most closely matches a portion of the intensity signals. For example, the transmittance measuring method and apparatus of this embodiment can convolve the intensity signals with a broad "W"-shaped function, an intermediate "W"-shaped function and a narrow "W"-shaped function. Thereafter, the portion of the intensity signals which most closely match one of the "W"-shaped patterns can be identified and subsequently analyzed as described above to measure the transmittance of the blood within the retinal vessel.

Once the intensity signals corresponding to light which has propagated through a retinal vessel are identified, the transmittance measuring method and apparatus 10 can determine an intensity profile function which compensates for reflections from the central portions of the retinal vessel and, in turn, can determine the transmittance of the blood within the retinal vessel. By compensating for reflections from the central portion of the retinal vessel and, in some embodiments, for reflections from the opposed edge portions of the retinal vessel, the transmittance measuring method and apparatus more precisely measures the transmittance of the blood within the retinal vessel. As a result, the other physiological parameters which can be determined based upon the transmittance measurement can also be more precisely defined, thereby permitting more accurate diagnosis and treatment of patients.

According to another advantageous embodiment outlined in FIG. 7, blood within a retinal vessel can be analyzed by providing a mathematical model of the intensity of light transmitted through the retinal vessel as a function of retinal vessel position. The mathematical model includes a plurality of parameters including parameters describing the blood within the retinal vessel, including the transmittance T of the blood, and parameters describing the retinal vessel, including the width or diameter of the retinal vessel at. According to the present invention, the mathematical model can also include parameters describing reflections of light from the retinal vessel which occurred prior to propagation of the light through the retinal vessel. For example, the mathematical model can include a parameter R defining the magnitude of reflections from central portions of the retinal vessel (the central reflection), a parameter $x_1$ defining the retinal vessel position at which the central reflection occurred, and a parameter $\sigma_1$ defining the width of the central reflection.

The mathematical model can also include parameters relating to the shape and size of the finite point spread function of the optical source 12. As a result, this advantageous method of the present invention can compensate for the finite point spread function of the incident light by properly constructing the mathematical model.

While a number of different mathematical models can be constructed without departing from the spirit and scope of the present invention, the mathematical model of one advantageous embodiment is as follows:

$$f(x) = (mx+b) - Te^{-\left(\frac{x-x_0}{\sigma_0}\right)^4} + Re^{-\left(\frac{x-x_1}{\sigma_1}\right)^2}$$

wherein the linear term (mx+b) defines a line constructed through the lateralmost points of the portion of the intensity profile function which corresponds to light that has propagated through a retinal vessel. In addition, x defines the retinal vessel position and the term $$Te^{-\left(\frac{x-x_0}{\sigma_0}\right)^4}$$

is a Gaussian subtract having a depth of T, a width of $\sigma_0$ and a position relative to the retinal vessel of $x_0$.

Following construction of the intensity profile function, the mathematical model is fit to the intensity profile function as shown in block 118 of FIG. 7. For example, the mathematical model typically defines a nonlinear curve as defined above which is fit to the intensity profile function. Based upon the fit of the mathematical model to the intensity profile function, the method of this advantageous embodiment can then determine at least one parameter describing the retinal vessel, such as the transmittance T of blood within the retinal vessel or the diameter $\sigma_0$ of the retinal vessel. See block 120 of FIG. 7.

Accordingly, the method of this alternative embodiment also determines retinal vessel parameters, such as the transmittance of blood within the retinal vessel, in an accurate manner by accounting for reflections from the retinal vessel in the mathematical model. As a result, the other physiological parameters which can be determined based upon the transmittance of blood within the retinal vessel can also be more precisely defined.

Many modifications and other embodiments of the invention will come to the mind of one skilled in the art to which this invention pertains who has the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A method of measuring the transmittance of blood within a retinal vessel, the method comprising the steps of:
   illuminating the retinal vessel and at least a portion of the background fundus within an eye;
   detecting the intensity of light reflected from illuminated portions of the eye;
   identifying a portion of the detected light intensities as corresponding to light that has been transmitted through a retinal vessel, wherein said identifying step comprises matching a portion of the detected light intensities with a predetermined pattern corresponding to the intensity of light that has propagated through a retinal vessel;
   constructing an intensity profile function based upon the identified portion of the detected light intensities, wherein the intensity profile function approximates the intensity of light transmitted through the retinal vessel as a function of retinal vessel position, and wherein said constructing step comprises compensating for at least some of the reflections of light from the retinal vessel which occurred prior to propagation of the light through the retinal vessel; and
   determining the transmittance of blood within the retinal vessel based upon the intensity profile function.

2. A method according to claim 1 wherein said constructing step further comprises determining the intensity of light transmitted through lateral portions of the retinal vessel, wherein said compensating step comprises compensating for reflections of light from a central portion of the retinal vessel which occurred prior to propagation of the light through the retinal vessel, and wherein said compensating step further comprises creating the intensity profile function based upon the intensity of light transmitted through the lateral portions of the retinal vessel such that the intensity profile function approximates the light transmitted through the central portion of the retinal vessel in the absence of reflections from the central portion of the retinal vessel.

3. A method according to claim 2 wherein said step of determining the intensity of light transmitted through lateral portions of the retinal vessel comprises approximating a portion of the intensity profile function describing the intensity of light transmitted through lateral portions of the retinal vessel as a function of retinal vessel position, and wherein said creating step comprises fitting a curve to the portion of the intensity profile function describing the intensity of light transmitted through lateral portions of the retinal vessel as a function of retinal vessel position such that the fitted curve defines the intensity profile function.

4. A method according to claim 1 wherein said illuminating step comprises illuminating the retinal vessel and at least a portion of the background fundus with light defined by a finite point spread function, and wherein said constructing step further comprises compensating for the finite point spread function of the light such that the transmittance of blood within the blood vessel is more accurately determined.

5. A method according to claim 1 wherein said matching step comprises matching a portion of the detected light intensities with a W-shaped pattern.

6. A method according to claim 1 wherein said matching step comprises comparing the detected light intensities with a plurality of different patterns corresponding to the intensity of light that has propagated through respective ones of a plurality of different retinal vessels.

7. A method of measuring the transmittance of blood within a retinal vessel, the method comprising the steps of:
   illuminating the retinal vessel and at least a portion of the background fundus within an eye;
   detecting the intensity of light reflected from illuminated portions of the eye;
   constructing an intensity profile function based upon the detected light intensity, wherein the intensity profile function approximates the intensity of light transmitted through the retinal vessel as a function of retinal vessel position, and wherein said constructing step comprises compensating for at least some of the reflections of light from the retinal vessel which occurred prior to propagation of the light through the retinal vessel;

constructing a second intensity profile function which defines a curve and approximates the intensity of light reflected from the background fundus as a function of retinal position; and determining the transmittance of blood within the retinal vessel based upon the intensity profile function, wherein said step of determining the transmittance of blood within the retinal vessel is based upon both the intensity profile function and the second intensity profile function.

8. A method according to claim 7 wherein said step of constructing a second intensity profile function comprises compensating for reflections of light at opposed edge portions of the retinal vessel.

9. A method according to claim 7 wherein said step of determining the transmittance of blood within the retinal vessel comprises:

dividing the intensity profile function by the second intensity profile function to form an intermediate transmittance function; and determining a minimum value of the intermediate transmittance function, wherein the minimum value corresponds to the transmittance of the blood within the retinal vessel.

10. A method of measuring the transmittance of blood within a retinal vessel based upon intensity signals representing the intensity of light reflected from illuminated portions of an eye including the retinal vessel and a background fundus, the method comprising the steps of:

matching a portion of the intensity signals with a predetermined pattern corresponding to the intensity of light that has propagated through a retinal vessel so as to identify that portion of the intensity signals that has been transmitted through a retinal vessel;

constructing an intensity profile function based upon the identified portion of the intensity signals representing the intensity of light reflected from illuminated portions of the eye, wherein the intensity profile function approximates the intensity of light transmitted through the retinal vessel as a function of retinal vessel position, and wherein said constructing step comprises compensating for at least some of the reflections of light from the retinal vessel which occurred prior to propagation of the light through the retinal vessel;

determining the intensity of light reflected from the background fundus based upon the intensity signals representing the intensity of light reflected from the background fundus; and determining the transmittance of blood within the retinal vessel based upon the intensity profile function and the intensity of light reflected from the background fundus.

11. A method according to claim 10 wherein said constructing step further comprises determining the intensity of light transmitted through lateral portions of the retinal vessel based upon the intensity signals representing the intensity of light transmitted through lateral portions of the retinal vessel, wherein said compensating step comprises compensating for reflections of light from a central portion of the retinal vessel which occurred prior to propagation of the light through the retinal vessel, and wherein said compensating step further comprises creating the intensity profile function based upon the intensity of light transmitted through lateral portions of the retinal vessel such that the intensity profile function approximates the light transmitted through the central portion of the retinal vessel in the absence of reflections from the central portion of the retinal vessel.

12. A method according to claim 11 wherein said step of determining the intensity of light transmitted through lateral portions of the retinal vessel comprises approximating a portion of the intensity profile function describing the intensity of light transmitted through lateral portions of the retinal vessel as a function of retinal vessel position, and wherein said creating step comprises fitting a curve to the portion of the intensity profile function describing the intensity of light transmitted through lateral portions of the retinal vessel as a function of retinal vessel position such that the fitted curve defines the intensity profile function.

13. A method according to claim 10 wherein the retinal vessel and at least a portion of the background fundus are illuminated with light defined by a finite point spread function, and wherein said constructing step further comprises compensating for the finite point spread function of the light such that the transmittance of blood within the blood vessel is more accurately determined.

14. A method according to claim 10 wherein said matching step comprises matching a portion of the detected light intensities with a W-shaped pattern.

15. A method according to claim 10 wherein said matching step comprises comparing the detected light intensities with a plurality of different patterns corresponding to the intensity of light that has propagated through respective ones of a plurality of different retinal vessels.

16. A method of measuring the transmittance of blood within a retinal vessel based upon intensity signals representing the intensity of light reflected from illuminated portions of an eye including the retinal vessel and a background fundus, the method comprising the steps of:

constructing an intensity profile function based upon the intensity signals representing the intensity of light reflected from illuminated portions of the eye, wherein the intensity profile function approximates the intensity of light transmitted through the retinal vessel as a function of retinal vessel position, and wherein said constructing step comprises compensating for at least some of the reflections of light from the retinal vessel which occurred prior to propagation of the light through the retinal vessel;

determining the intensity of light reflected from the background fundus based upon the intensity signals representing the intensity of light reflected from the background fundus, wherein said step of determining the intensity of light reflected from the background fundus comprises constructing a second intensity profile function which defines a curve and approximates the intensity of light reflected from the background fundus as a function of retinal position; and determining the transmittance of blood within the retinal vessel based upon the intensity profile function and the second intensity profile function.

17. A method according to claim 16 wherein said step of constructing a second intensity profile function comprises constructing a linear function which approximates the intensity of light reflected from the background fundus as a function of retinal position.

18. A method according to claim 16 wherein said step of constructing a second intensity profile function comprises compensating for reflections of light at opposed edge portions of the retinal vessel.

19. A method according to claim 16 wherein said step of determining the transmittance of blood within the retinal vessel comprises the steps of:

dividing the intensity profile function by the second intensity profile function to form an intermediate transmittance function; and determining a minimum value of the intermediate transmittance function, wherein the minimum value corresponds to the transmittance of the blood within the retinal vessel.

20. A method of constructing an intensity profile function based upon intensity signals representing the intensity of light reflected from illuminated portions of an eye including a retinal vessel and a background fundus, wherein the intensity profile function approximates the intensity of light transmitted through a retinal vessel as a function of retinal vessel position, the method comprising the steps of:

determining the intensity of light transmitted through lateral portions of the retinal vessel based upon intensity signals representing the intensity of light reflected from illuminated portions of the eye, wherein said determining step comprises approximating a portion of the intensity profile function describing the intensity of light transmitted through lateral portions of the retinal vessel as a function of retinal vessel position; and compensating for reflections of light from a central portion of the retinal vessel which occurred prior to propagation of the light through the retinal vessel, wherein said compensating step comprises creating the intensity profile function based upon the intensity of light transmitted through the lateral portions of the retinal vessel such that the intensity profile function approximates the light transmitted through the central portion of the retinal vessel in the absence of reflections from the central portion of the retinal vessel, wherein said creating step comprises fitting a cubic function to the portion of the intensity profile function describing the intensity of light transmitted through lateral portions of the retinal vessel as a function of retinal vessel position.

21. A method according to claim 18 wherein said fitting step comprises fitting a substantially U-shaped curve to the portion of the intensity profile function describing the intensity of light transmitted through lateral portions of the retinal vessel as a function of retinal vessel position.

22. A method of analyzing blood within a retinal vessel based upon intensity signals representing the intensity of light reflected from illuminated portions of an eye including the retinal vessel and a background fundus, the method comprising the steps of:

constructing an intensity profile function based upon the intensity signals representing the intensity of light reflected from illuminated portions of the eye, wherein the intensity profile function approximates the intensity of light transmitted through the retinal vessel as a function of retinal vessel position;

providing a mathematical model of the intensity of light transmitted through the retinal vessel as a function of retinal vessel position, wherein the mathematical model is a cubic function that includes a plurality of parameters including parameters describing the retinal vessel and parameters describing reflections of light from the retinal vessel which occurred prior to propagation of the light through the retinal vessel;

fitting the mathematical model to a portion of the intensity profile function that describes the intensity of light transmitted through lateral portions of the retinal vessel as a function of retinal vessel position; and determining at least one parameter describing the retinal vessel following said fitting step.

23. A method according to claim 22 wherein the mathematical model includes a parameter defining the transmittance of blood within the retinal vessel, and wherein said determining step comprises approximating the transmittance of blood within the retinal vessel.

24. A method according to claim 22 wherein the mathematical model includes a parameter defining the diameter of the retinal vessel, and wherein said determining step comprises approximating the diameter of the retinal vessel.

25. An apparatus for measuring the transmittance of blood within a retinal vessel, the apparatus comprising:

an optical source for illuminating the retinal vessel and at least a portion of the background fundus within an eye;

a detector for measuring the intensity of light reflected from the illuminated portions of the eye;

means, responsive to said detector, for matching a portion of the measured light intensities with a predetermined pattern corresponding to the intensity of light that has propagated through a retinal vessel so as to identify that portion of the intensity signals that has been transmitted through a retinal vessel;

means, responsive to said detector, for constructing an intensity profile function based upon the matching portion of the measured light intensities, wherein the intensity profile function approximates the intensity of light transmitted through the retinal vessel as a function of retinal vessel position, and wherein said constructing means comprises means for compensating for at least some of the reflections of light from the retinal vessel produced prior to propagation of the light through the retinal vessel; and means, responsive to said constructing means, for determining the transmittance of blood within the retinal vessel based upon the intensity profile function.

26. An apparatus according to claim 25 wherein said constructing means further comprises means for determining the intensity of light transmitted through lateral portions of the retinal vessel, wherein said compensating means comprises means for compensating for reflections of light from a central portion of the retinal vessel which occurred prior to propagation of the light through the retinal vessel, and wherein said compensating means further comprises means for creating the intensity profile function based upon the intensity of light transmitted through the lateral portions of the retinal vessel such that the intensity profile function approximates the light transmitted through the central portion of the retinal vessel in the absence of reflections from the central portion of the retinal vessel.

27. An apparatus according to claim 26 wherein said means for determining the intensity of light transmitted through lateral portions of the retinal vessel comprises means for approximating a portion of the intensity profile function describing the intensity of light transmitted through lateral portions of the retinal vessel as a function of retinal vessel position, and wherein said creating means comprises means for fitting a curve to the portion of the intensity profile function describing the intensity of light transmitted through lateral portions of the retinal vessel as a function of retinal vessel position such that the fitted curve defines the intensity profile function.

28. An apparatus according to claim 25 wherein said optical source illuminates the retinal vessel and at least a portion of the background fundus with light defined by a finite point spread function, and wherein said constructing means further comprises means for compensating for the finite point spread function of the light such that the transmittance of blood within the blood vessel is more accurately determined.

29. An apparatus according to claim 25 wherein said means for matching comprises means for matching a portion of the detected light intensities with a W-shaped pattern.

30. An apparatus according to claim 25 wherein said means for matching comprises means for comparing the detected light intensities with a plurality of different patterns corresponding to the intensity of light that has propagated through respective ones of a plurality of different retinal vessels.

31. An apparatus for measuring the transmittance of blood within a retinal vessel, the apparatus comprising:

an optical source for illuminating the retinal vessel and at least a portion of the background fundus within an eye;

a detector for measuring the intensity of light reflected from the illuminated portions of the eye;

means, responsive to said detector, for constructing an intensity profile function based upon the measured light intensities, wherein the intensity profile function approximates the intensity of light transmitted through the retinal vessel as a function of retinal vessel position, and wherein said constructing means comprises means for compensating for at least some of the reflections of light from the retinal vessel produced prior to propagation of the light through the retinal vessel;

means, responsive to said detector, for constructing a second intensity profile function which defines a curve and approximates the intensity of light reflected from the background fundus as a function of retinal position; and means, responsive to said constructing means, for determining the transmittance of blood within the retinal vessel is based upon both the intensity profile function and the second intensity profile function.

32. An apparatus according to claim 31 wherein said means for constructing a second intensity profile function comprises means for compensating for reflections of light at opposed edge portions of the retinal vessel.

33. An apparatus according to claim 31 wherein said means for determining the transmittance of blood within the retinal vessel comprises:

means for dividing the intensity profile function by the second intensity profile function to form an intermediate transmittance function; and means, responsive to said dividing means, for determining a minimum value of the intermediate transmittance function, wherein the minimum value corresponds to the transmittance of the blood within the retinal vessel.

34. A computer program product for determining the transmittance of blood within a retinal vessel based upon intensity signals representing the intensity of light reflected from illuminated portions of an eye including the retinal vessel and a background fundus, the computer program product comprising a computer-readable storage medium having computer-readable program code means embodied in said medium, said computer-readable program code means comprising:

first computer-readable program code means for constructing an intensity profile function based upon the intensity signals representing the intensity of light reflected from the illuminated portions of the eye, wherein the intensity profile function approximates the intensity of light transmitted through the retinal vessel as a function of retinal vessel position, wherein said first computer-readable program code means comprises computer-readable program code means for compensating for at least some of the reflections of light from the retinal vessel which occurred prior to propagation of the light through the retinal vessel;

second computer-readable program code means for determining the intensity of light reflected from the background fundus based upon the intensity signals representing the intensity of light reflected from the background fundus, wherein said second computer-readable program code means for determining the intensity of light reflected from the background fundus comprises computer-readable program code means for constructing a second intensity profile function which defines a curve and approximates the intensity of light reflected from the background fundus as a function of retinal position; and third computer-readable program code means for determining the transmittance of blood within the retinal vessel based upon the intensity profile function constructed by said first computer-readable program code means and the second intensity profile function constructed by said second computer-readable program code means.

35. A computer program product according to claim 34 wherein said first computer-readable program code means further comprises computer-readable program code means for determining the intensity of light transmitted through lateral portions of the retinal vessel based upon the intensity signals representing the intensity of light transmitted through lateral portions of the retinal vessel, wherein said computer-readable program code means for compensating for at least some of the reflections from the retinal vessel comprises computer-readable program code means for compensating for reflections of light from a central portion of the retinal vessel which occurred prior to propagation of the light through the retinal vessel, and wherein said computer-readable program code means for compensating for reflections of light from a central portion of the retinal vessel comprises computer-readable program code means for creating the intensity profile function based upon the intensity of light transmitted through the lateral portions of the retinal vessel such that the intensity profile function approximates the light transmitted through the central portion of the retinal vessel in the absence of reflections from the central portion of the retinal vessel.

36. A computer program product according to claim 35 wherein said computer-readable program code means for determining the intensity of light transmitted through lateral portions of the retinal vessel comprises computer-readable program code means for approximating a portion of the intensity profile function describing the intensity of light transmitted through lateral portions of the retinal vessel as a function of retinal vessel position, and wherein computer-readable program code means for creating the intensity profile function comprises computer-readable program code means for fitting a curve to the portion of the intensity profile function describing the intensity of light transmitted through lateral portions of the retinal vessel as a function of retinal vessel position such that the fitted curve defines the intensity profile function.

37. A computer program product according to claim 34 wherein said computer-readable program code means for constructing a second intensity profile function comprises computer-readable program code means for compensating for reflections of light at opposed edge portions of the retinal vessel.

38. A computer program product according to claim 34 wherein said second computer-readable program code means for determining the transmittance of blood within the retinal vessel comprises:

computer-readable program code means for dividing the intensity profile function by the second intensity profile function to form an intermediate transmittance function; and computer-readable program code means for determining a minimum value of the intermediate transmittance function, wherein the minimum value corresponds to the transmittance of the blood within the retinal vessel.

39. A computer program product according to claim 34 wherein the retinal vessel and at least a portion of the background fundus are illuminated with light defined by a finite point spread function, and wherein said first computer-readable program code means further comprises computer-readable program code means for compensating for the finite point spread function of the light such that the transmittance of blood within the blood vessel is more accurately determined.

\* \* \* \* \*

UNITED STATES PATENT AND TRADEMARK OFFICE
CERTIFICATE OF CORRECTION

PATENT NO. : 5,935,076

DATED : August 10, 1999

INVENTOR(S) : Smith et al.

It is certified that error appears in the above-identified patent and that said Letters Patent is hereby corrected as shown below:

Column 19, line 35, "claim 18" should read --claim 20--.

Signed and Sealed this

Twenty-eighth Day of December, 1999

Attest:

Q. TODD DICKINSON

*Attesting Officer*    *Acting Commissioner of Patents and Trademarks*